United States Patent

Ruth et al.

(10) Patent No.: US 9,377,386 B2
(45) Date of Patent: Jun. 28, 2016

(54) IMPACT TESTER HAVING A SAFETY RETURN ARM

(71) Applicant: Tinius Olsen Testing Machine Company, Horsham, PA (US)

(72) Inventors: Earl A. Ruth, Sellersville, PA (US); John C. Ivory, Horley (GB)

(73) Assignee: TINIUS OLSEN TESTING MACHINE COMPANY, Horsham, PA (US)

( * ) Notice: Subject to any disclaimer, the term of this patent is extended or adjusted under 35 U.S.C. 154(b) by 135 days.

(21) Appl. No.: 14/463,374

(22) Filed: Aug. 19, 2014

(65) Prior Publication Data

US 2015/0052972 A1 Feb. 26, 2015

Related U.S. Application Data

(60) Provisional application No. 61/869,107, filed on Aug. 23, 2013.

(51) Int. Cl.
| | |
|---|---|
| *G01N 3/32* | (2006.01) |
| *G01N 3/00* | (2006.01) |
| *G01N 33/00* | (2006.01) |
| *G01N 15/00* | (2006.01) |
| *G01N 3/30* | (2006.01) |
| *G01N 3/303* | (2006.01) |

(52) U.S. Cl.
CPC .................. *G01N 3/30* (2013.01); *G01N 3/303* (2013.01); *G01N 2203/0039* (2013.01); *G01N 2203/0098* (2013.01)

(58) Field of Classification Search
None
See application file for complete search history.

(56) References Cited

U.S. PATENT DOCUMENTS

| | | | | | |
|---|---|---|---|---|---|
| 2,388,246 | A | * | 11/1945 | Berger | G01N 3/30 73/12.14 |
| 3,209,585 | A | * | 10/1965 | Wolstenholme | G01N 3/066 73/12.14 |
| 3,583,215 | A | * | 6/1971 | Franz | G01N 3/30 73/12.14 |
| 4,576,034 | A | * | 3/1986 | Ferree | G01N 29/223 367/13 |
| 5,390,534 | A | * | 2/1995 | Feeney | G01N 3/30 73/12.14 |
| 5,922,937 | A | * | 7/1999 | Kowalski | G01N 3/30 73/12.13 |

(Continued)

FOREIGN PATENT DOCUMENTS

DE 102010037979 A1 † 4/2012
SU 1080066 A1 † 12/1989

OTHER PUBLICATIONS

Zwick, Impact Strength Testing of Izod Plastic Specimen, Integrated Notch Milling Unit, Automated, Tempered, published Jun. 10, 2010 at https://www.youtube.com/watch?v=qXpYc5DEid0.†
Zwick, Tensile, Bending, Impact Test on Plastics, Automated, Polar-type, published Jun. 29, 2010 at https://www.youtube.com/watch?v=NC63y6OWAxc.†

(Continued)

*Primary Examiner* — Peter Macchiarolo
*Assistant Examiner* — Jermaine Jenkins
(74) *Attorney, Agent, or Firm* — Morgan, Lewis & Bockius LLP

(57) ABSTRACT

An impact tester includes a pendulum rotatable about a first axis from a latched position to an impact position. The pendulum is configured to impact a test specimen in the impact position. A safety return arm is rotatable about a second axis generally parallel to the first axis. The safety return arm is configured to lift the pendulum to the latched position, allow the pendulum to swing from the latched position toward the impact position, and selectively stop the pendulum between the latched position and the impact position.

26 Claims, 8 Drawing Sheets

(56) References Cited

U.S. PATENT DOCUMENTS

| | | | |
|---|---|---|---|
| 6,990,845 B2 * | 1/2006 | Voon | G01N 3/48 73/12.14 |
| 7,360,393 B1 * | 4/2008 | Abke | G01M 7/08 73/12.14 |
| 7,516,646 B2 * | 4/2009 | Makimoto | G01M 7/08 73/12.12 |

OTHER PUBLICATIONS

Zwick, Material to the Test, published Mar. 1, 2007 by Quality Engineering, published at http://www.qe-online.de/artikelarchiv/-/journal_content/56/12275/384345/Material-im-H%C3%A4rtetest/.†

\* cited by examiner
† cited by third party

IMPACT TESTER HAVING A SAFETY RETURN ARM

CROSS-REFERENCE TO RELATED APPLICATIONS

This application claims the benefit of U.S. Provisional Patent Application No. 61/869,107 filed Aug. 23, 2013 entitled "Impact Tester", which is incorporated by reference herein in its entirety.

BACKGROUND OF THE INVENTION

The present invention generally relates to impact testers, and particularly to impact testers having a safety mechanism.

Impact tests are laboratory tests performed to measure the response of a material to dynamic loading. The most common laboratory test configurations are the pendulum machine and the drop tower.

Pendulum machines include a pendulum of known mass and length that is released from a known height to impact a sample of material. During the fall from its raised position, the pendulum's potential energy decreases, changing into kinetic energy. The difference between the pendulum height at the moment of release and the maximum height attained after fracturing the specimen is a measure of the impact energy absorbed by the specimen.

Impact testing machines are typically of the Charpy type, the Izod type, tension impact or shear impact testing type. These various types of impact testing machines differ from one another primarily in the shape of the specimen, in the way in which the specimen is held at the moment of fracture, and in the shape of the hammer striking edge.

BRIEF SUMMARY OF THE INVENTION

In one embodiment there is an impact tester comprising: a pendulum rotatable about a first axis from a latched position to an impact position, the pendulum configured to impact a test specimen in the impact position; and a safety return arm rotatable about a second axis generally parallel to the first axis, the safety return arm configured to lift the pendulum to the latched position, allow the pendulum to swing from the latched position toward the impact position, and selectively stop the pendulum between the latched position and the impact position.

In a further embodiment, the impact tester comprises a motor configured to control an angular position of the safety return arm. In a further embodiment, the impact tester comprises a first sensor configured to measure an angular position of the pendulum; a second sensor configured to measure an angular position of the safety return arm; and a control system configured to control the angular position of the pendulum using the safety return arm based on the angular position of the pendulum and the angular position of the safety return arm. In a further embodiment, the impact tester comprises a frame supporting the pendulum and the safety return arm, wherein the first sensor is configured to measure the angular position of the pendulum relative to the frame.

In one embodiment, measurements from the first and second sensors are used to determine the position of the safety return arm relative to the pendulum. In one embodiment, the second sensor is configured to measure the position of the safety return arm relative to the frame. In a further embodiment, the impact tester comprises a user interface configured to control the control system. In one embodiment, the safety return arm includes a lift member that is configured to engage a right side surface of the pendulum when lifting and stopping the pendulum. In one embodiment, the lift member includes an elastomeric bumper. In one embodiment, a proximal end of the safety return arm is axially spaced from a proximal end of the pendulum and the lift member travels on the same plane as the pendulum. In one embodiment, the safety return arm includes a stop member that is configured to engage a left side surface of the pendulum and limit the pendulum from swinging back toward the latch position after impacting the test specimen.

In one embodiment, the stop member includes an elastomeric bumper. In one embodiment, the stop member and the pendulum travel on the same plane. In a further embodiment, the impact tester comprises a sensor configured to detect the presence of an object proximate a swing path of the pendulum. In one embodiment, the sensor is a light curtain. In one embodiment, the pendulum is rotatable about the first axis from the latched position through the impact position to a post-impact position and the safety return arm is configured to selectively stop the pendulum between the latched position and the post-impact position. In one embodiment the first axis is coaxial with the second axis. In one embodiment, the pendulum is configured to perform Charpy impact testing of the test specimen. In one embodiment, the pendulum is configured to perform Izod impact testing of the test specimen. In one embodiment, the pendulum includes a crosshead configured to perform tension impact testing of the test specimen. In one embodiment, the pendulum is configured to perform shear impact testing of the test specimen.

BRIEF DESCRIPTION OF THE SEVERAL VIEWS OF THE DRAWINGS

The following detailed description of embodiments of an impact tester, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 2:
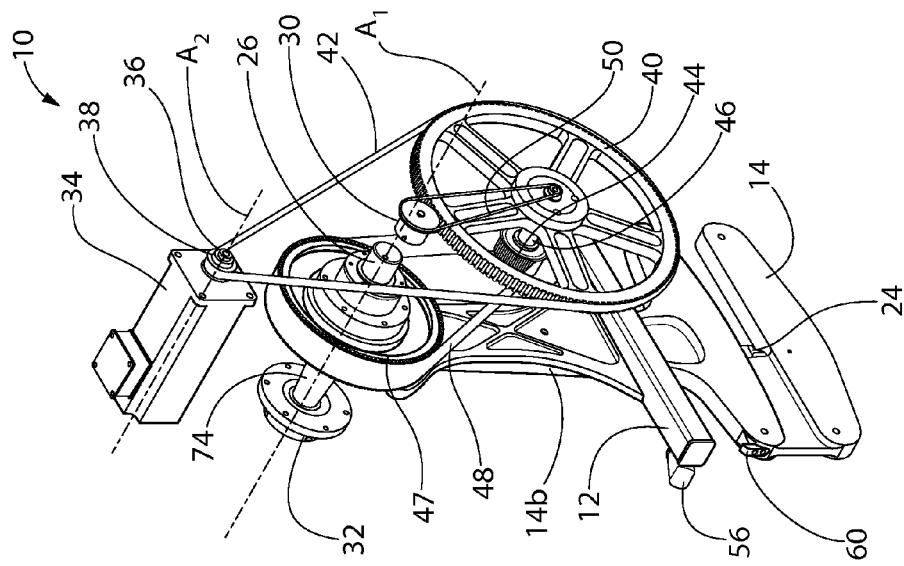
FIG. 2 is a rear, left, top isometric view of the impact tester of FIG. 1 shown with the frame and base removed for clarity.

Pendulum impact testing machines have a swinging mass that has the potential to injure an operator. Furthermore, lifting the pendulum back to the initial, latched position requires a certain amount of strength depending on the capacity of the machine and may further expose the operator to injuries.

Return arms, for lifting the pendulum into place, have been employed in the past but they have limitations. One limitation is that the return arm must move clear of the area of swing of the pendulum prior to performing a test. As such, the return arm is not in a position to quickly stop the pendulum mid-swing should there be a need.

Another limitation of a typical return arm is that it cannot catch the pendulum on a forward swing to prevent the pendulum from swinging back through the impact position where the specimen was broken. This is important for Izod testing when specimens do not completely break as swinging back into the partially broken specimen prevents the operator from properly evaluating and reporting the type of break the specimen has incurred.

Certain testing machines have included a clutch to connect the pendulum shaft to a motor that can stop the pendulum mid-swing if necessary for safety reasons and return the pendulum to the latch point. However, there are several problems with this technique.

Typically, a clutch needs to be engaged by spring force and disengaged by some other means to have a fail-safe stopping mechanism. This type of clutch, particularly for large machines, gets very large, expensive, and is not readily available. If this type of clutch is not used, then an enclosure must be used that locks closed while the pendulum is swinging. This may be problematic in certain testing situations where the operator must get a sample to be tested from a cooling bath, into the machine, and test the specimen within a short period of time (e.g., 5 seconds). The operator must also open and close a door of the safety enclosure for each test which adds to operator time and fatigue.

Clutches are also prone to dragging and not being completely friction free. If the clutch imparts any friction at all to the pendulum during a test, the test results may be erroneously high and invalidate the test results. This problem may not be evident to an operator who may continue to test numerous specimens and unknowingly report the erroneous data. Clutches may also absorb oil and grease over time which causes them to lose strength, sometimes to the point that they can no longer latch the pendulum. This then becomes an additional safety issue and results in additional maintenance and repair.

Further, the clutch is often permanently attached to the pendulum. Pendulum impact testers are typically designed such that they strike the specimen at the center-of-percussion of the pendulum to minimize energy losses to the machine that would be erroneously recorded as energy delivered to the specimen. Clutches mounted to the shaft of the pendulum may affect the mass distribution of the pendulum and therefore the pendulum's center-of-percussion. Even though one can account for the mass of the clutch in the design of the pendulum and keep the center-of-percussion at the correct point, the additional mass being far from the point of impact, may cause the pendulum to vibrate during a test and absorb energy which is erroneously reported as energy absorbed by the test specimen.

Referring to the drawings in detail, wherein like reference numerals indicate like elements throughout, there is shown in FIGS. 1-8B an impact tester, generally designated 10, in accordance with an exemplary embodiment of the present invention.

Impact tester 10 includes a safety return arm 12 that is configured to lift a pendulum 14 into position as well act as a safety device to impede the swinging pendulum 14 to prevent injury and/or damage to a test specimen within the swinging plane or swing path of pendulum 14. In one embodiment, safety return arm 12 allows pendulum 14 to swing freely with no added resistance or interference from the initial position toward the impact position, lift pendulum 14 back up to the initial or latched position and stop and/or limit pendulum 14 from swinging mid swing. In one embodiment, safety return arm 12 is configured to stop and retain pendulum 14 mid swing at any point during its forward or backward swing.

Pendulum 14 is configured to dynamically impact a test specimen to determine characteristics of the material such as flexibility, toughness, temperature-dependent ductile-brittle transition, and impact resistance such as shear impact resistance and tension impact resistance.

Impact tester 10 may be configured to perform one or more types of impact tests. Impact tester 10 may be a pendulum machine. In one embodiment, impact tester 10 is configured to perform Charpy impact testing of the test specimen. In one embodiment, impact tester 10 is configured to perform Izod impact testing of the test specimen. In one embodiment, impact tester 10 includes a crosshead configured to perform tension impact testing of the test specimen. In one embodiment, impact tester 10 is configured to perform shear impact testing of the test specimen. In alternative embodiments, impact tester 10 is a drop tower with the pendulum 14 discussed herein being replaced with a mass that is raised and dropped along a vertical, linear path.

Figure 1:
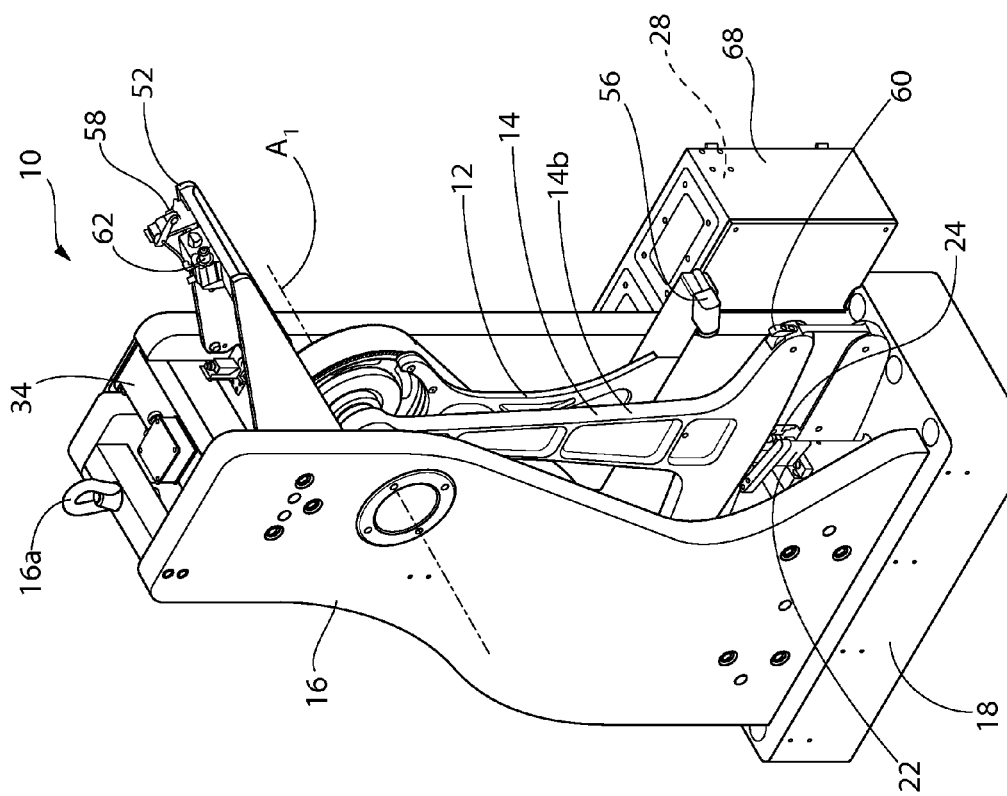
FIG. 1 is a front, left, top isometric view of an impact tester in accordance with an exemplary embodiment of the present invention shown with the pendulum in the impact position.

Referring to FIG. 1, a frame 16 may support pendulum 14 and safety return arm 12. Frame 16 may be supported by a base 18 that provides a rigid foundation. In one embodiment, base 18 is weighted and/or secured to prevent impact tester 10 from moving. Frame 16 may include a mount 16a such as an eyelet to allow for impact tester 10 to be lifted and moved. One or more anvils may be positioned on the base 18 and configured to hold a specimen of material to be tested. One or more shrouds 22 may be provided proximate the specimen to help minimize the amount of fragments from projecting from impact tester 10 during use. The anvil and shrouds may be replaceable should they become worn or replaceable with a different configuration to perform a different test. Frame 16 and base 18 may include a space that allows pendulum 14 and safety return arm 12 to rotate about an axis $A_1$ and along a plane perpendicular to axis $A_1$. The test specimen is placed on the anvil such that it intersects the plane perpendicular to axis $A_1$ and the pendulum contacts the test specimen in an impact position (FIG. 1).

Pendulum 14 may include an impact member 24 that contacts the test specimen in the impact position. In one embodiment, impact member 24 includes a blade with a pointed edge. In other embodiments, impact member 24 includes rounded tip, a crosshead tip or a pointed tip depending on the impact test being performed.

In one embodiment, pendulum 14 is weighted proximate a distal end such that pendulum 14 swings and impacts the test specimen with the desired amount of force generated by the swing of pendulum 14. Referring to FIG. 2, pendulum 14 may be coupled to an axle 74 and rotatable about axis $A_1$. Axle 74 may extend between opposing sides of frame 16. Safety return arm 12 may also be coupled to axle 74 and rotatable about axis $A_1$ such that pendulum 14 and safety return arm 12 are rotatable about coaxial, or the same, axis $A_1$. In other embodiments, safety return arm 12 and pendulum 14 are rotatable about different but parallel axes. In one embodiment, pendulum 14 is coupled to axle 74 such that axle 74 and pendulum 14 rotate together and safety return arm 12 rotates relative to axle 74. In another embodiment, axle 74 rotates with safety return arm 12 and pendulum 14 rotates relative to axle 74. In another embodiment, both safety return arm 12 and pendulum 14 rotate relative to axle 74. Axle 74 may be coupled to frame 16 using one or more bearings 32. Safety return arm 12 may be coupled to axle 74 axially adjacent to pendulum 14 but at least a portion of safety return arm 12 rotates along a plane coplanar with at least a portion of pendulum 14 as discussed in further detail below.

Referring to FIG. 2, pendulum 14 is generally freely (not including resistance from any bearings) rotatable about axis $A_1$ such that pendulum 14 swings by the force of gravity. In other embodiments, pendulum 14 includes intended resistance (such as a brake, clutch or gearing) and/or is coupled to a motor to provide a swinging force and/or a resistance to the swinging force. Safety return arm 12 may be rotatable about axis $A_1$ and also coupled to a control mechanism 28 (see FIGS. 1, 8B and 9). Control mechanism 28 may include a processor and associated hardware and software configured to control the angular position of pendulum 14 by moving safety return arm 12. In one embodiment, control mechanism 28 is configured to move safety return arm 12 based on the angular position of pendulum 14.

Control mechanism 28 may be configured to control a motor 34 coupled to safety return arm 12. The operation of motor 34 may be reversible such that the motion of safety return arm 12 may be controlled in both directions. Motor 34 may be coupled to safety return arm 12 by any desirable configuration. In one embodiment, a first gear 36 mounted on output motor axle 38 of motor 34 is coupled to a second gear 40 by a first belt 42. Second gear 40 may be coupled to a third gear 44 sharing a common axle 46. Third gear 44 may be coupled to a fourth gear 47 on the safety return arm 12 by a second belt 48.

Referring to FIG. 2, impact tester 10 may include a first sensor 30 configured to measure the angular position of the safety return arm 12 and a second sensor 26 configured to measure the angular position of pendulum 14. In one embodiment, first and second sensors 30, 26 are digital rotary encoders. Any sensors capable of measuring the position of safety return arm 12 and pendulum 14 may be used, such as proximity sensors. First sensor 30 may be coupled to safety return arm 12 by a third belt 50 coupled to the second gear 40. Second sensor 26 may be coupled to axle 74 which rotates with pendulum 14. Second sensor 26 may be configured to measure the position of pendulum 14 relative to a reference such as frame 16 and first sensor 30 may be configured to measure the angular position of safety return arm 12 relative to the reference such as frame 16. In one embodiment, second sensor 26 is configured to measure the position of pendulum 14 relative to a reference such as frame 16 and first sensor 30 is configured to measure the angular position of safety return arm 12 relative to pendulum 14. In one embodiment, first sensor 30 is configured to measure the angular position of safety return arm 12 relative to a reference such as frame 16 and second sensor 26 is configured to measure the position of pendulum 14 relative to safety return arm 12. The input from first sensor 30 and second sensor 26 may be used to calculate the position of safety return arm 12 relative to pendulum 14. The movement of safety return arm 12 during a test may therefore be based on the movement of pendulum 14. In one embodiment, motor 34 and sensors 30, 26 allow for proportional, integral, derivative, closed loop control of safety return arm 12. The movement of safety return arm 12 based on the movement of pendulum 14 may be suspended when desirable for safety return arm 12 to stop movement of pendulum 14.

Figure 3:
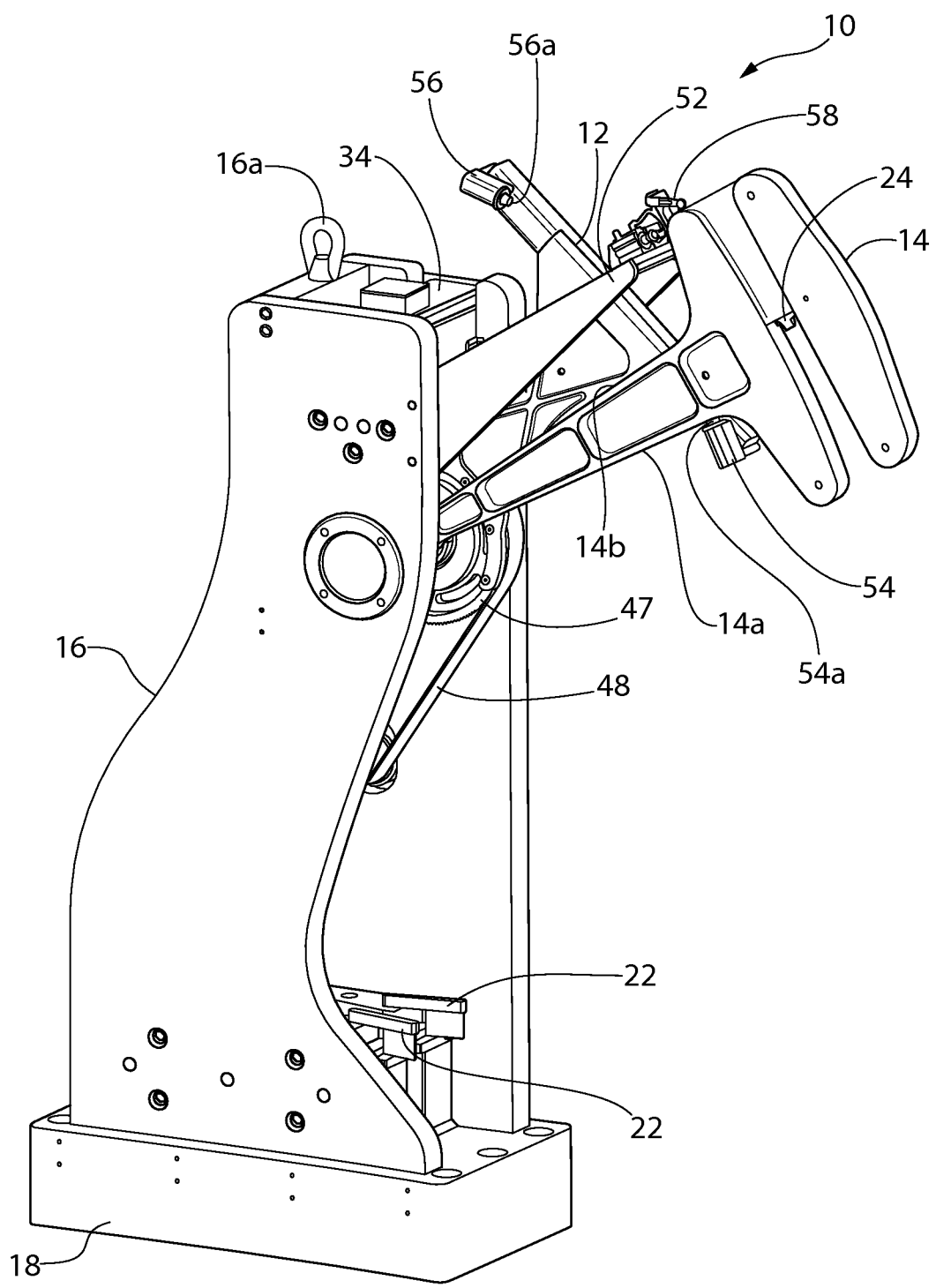
FIG. 3 is a front, left, top isometric view of the impact tester of FIG. 1 shown with the pendulum in the latched position and the safety return arm in the lift position.
Figure 4:
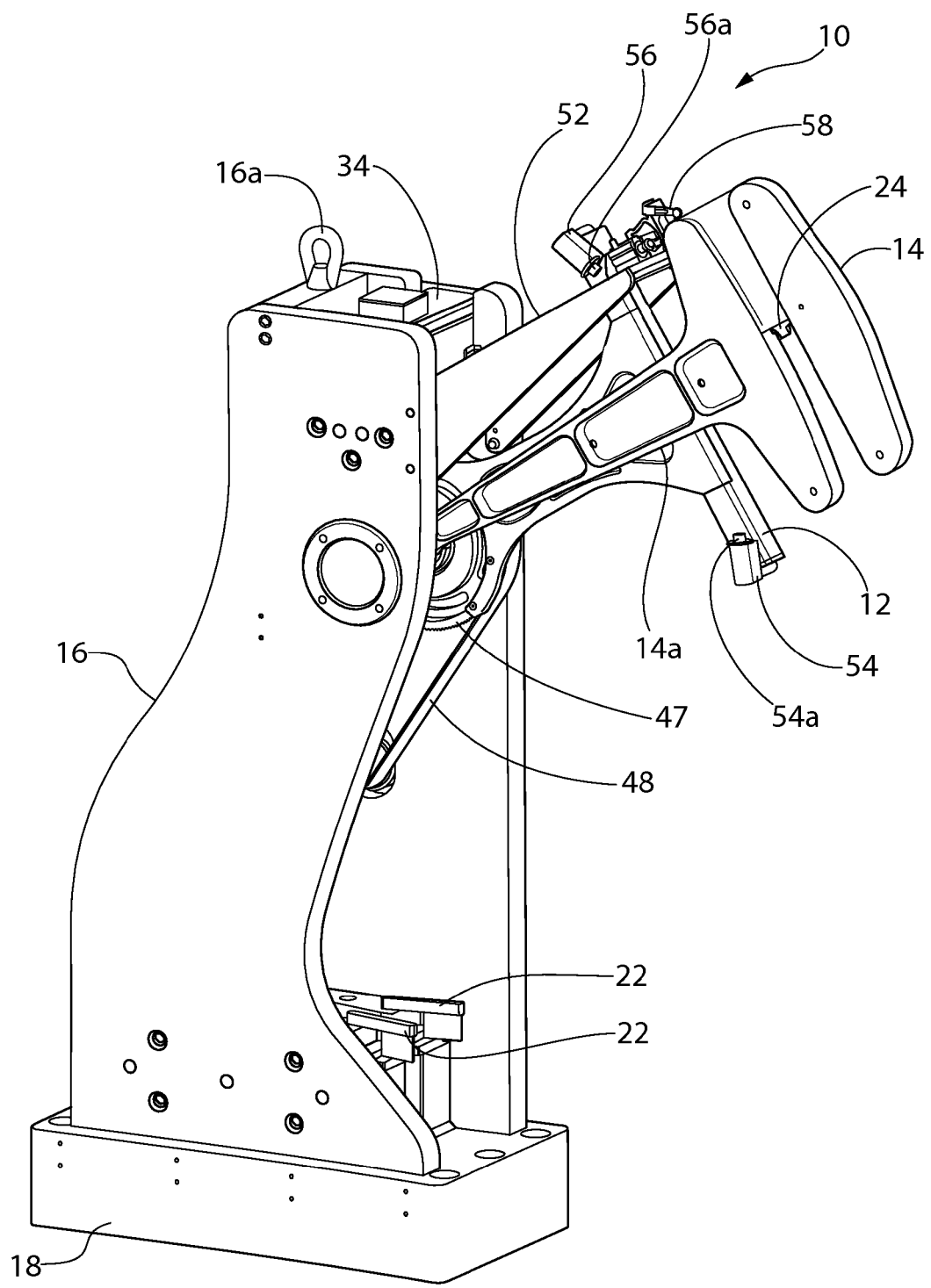
FIG. 4 is a front, left, top isometric view of the impact tester of FIG. 1 shown with the pendulum in the latched position and the safety return arm in the ready to be released position.
Figure 5:
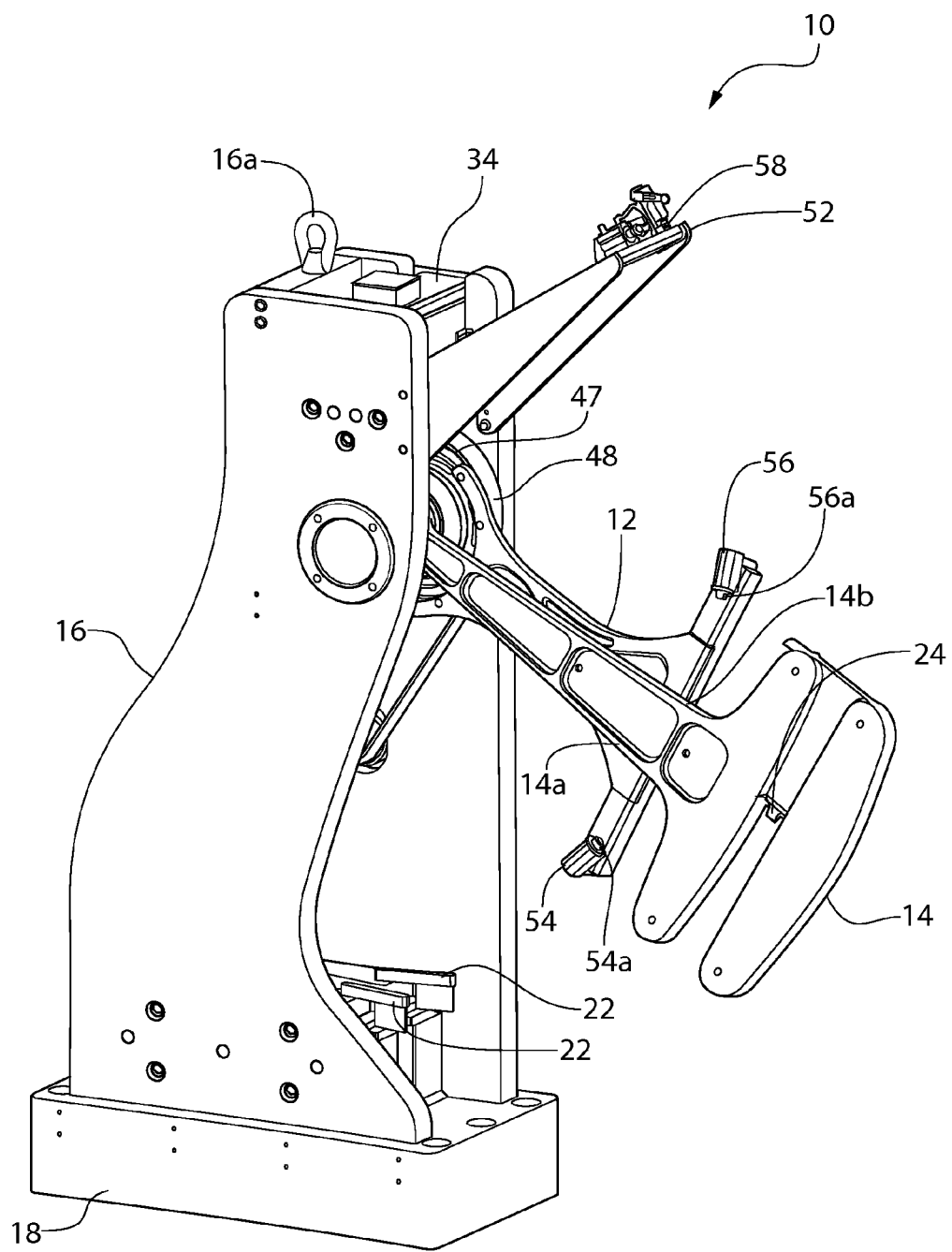
FIG. 5 is a front, left, top isometric view of the impact tester of FIG. 1 shown with the pendulum swinging from the latched position toward the impact position and the safety return arm following the pendulum.
Figure 6:
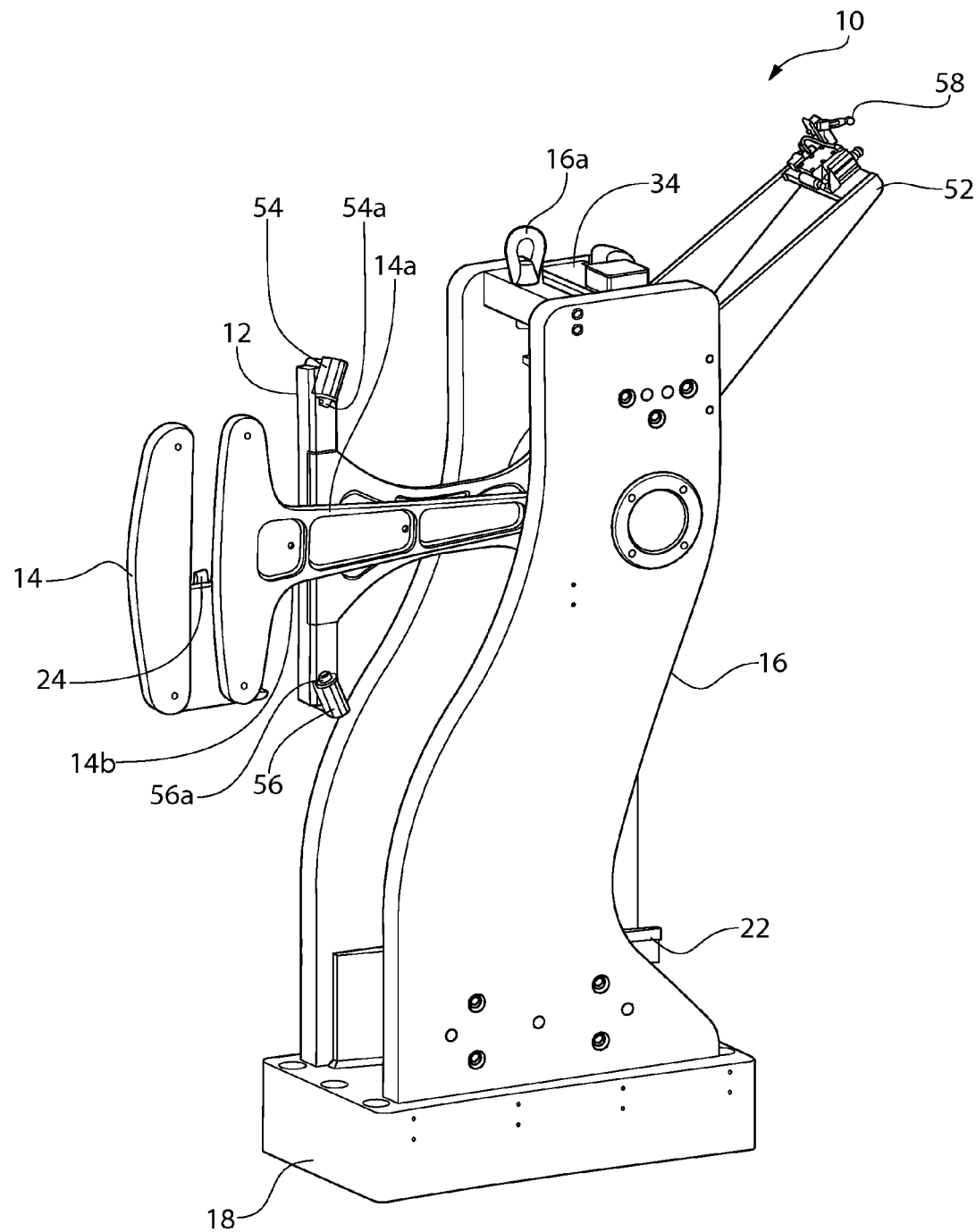
FIG. 6 is a front, right, top isometric view of the impact tester of FIG. 1 shown with the pendulum after swinging through the impact position to a maximum swing through position and the safety return arm following the pendulum.
Figure 7:
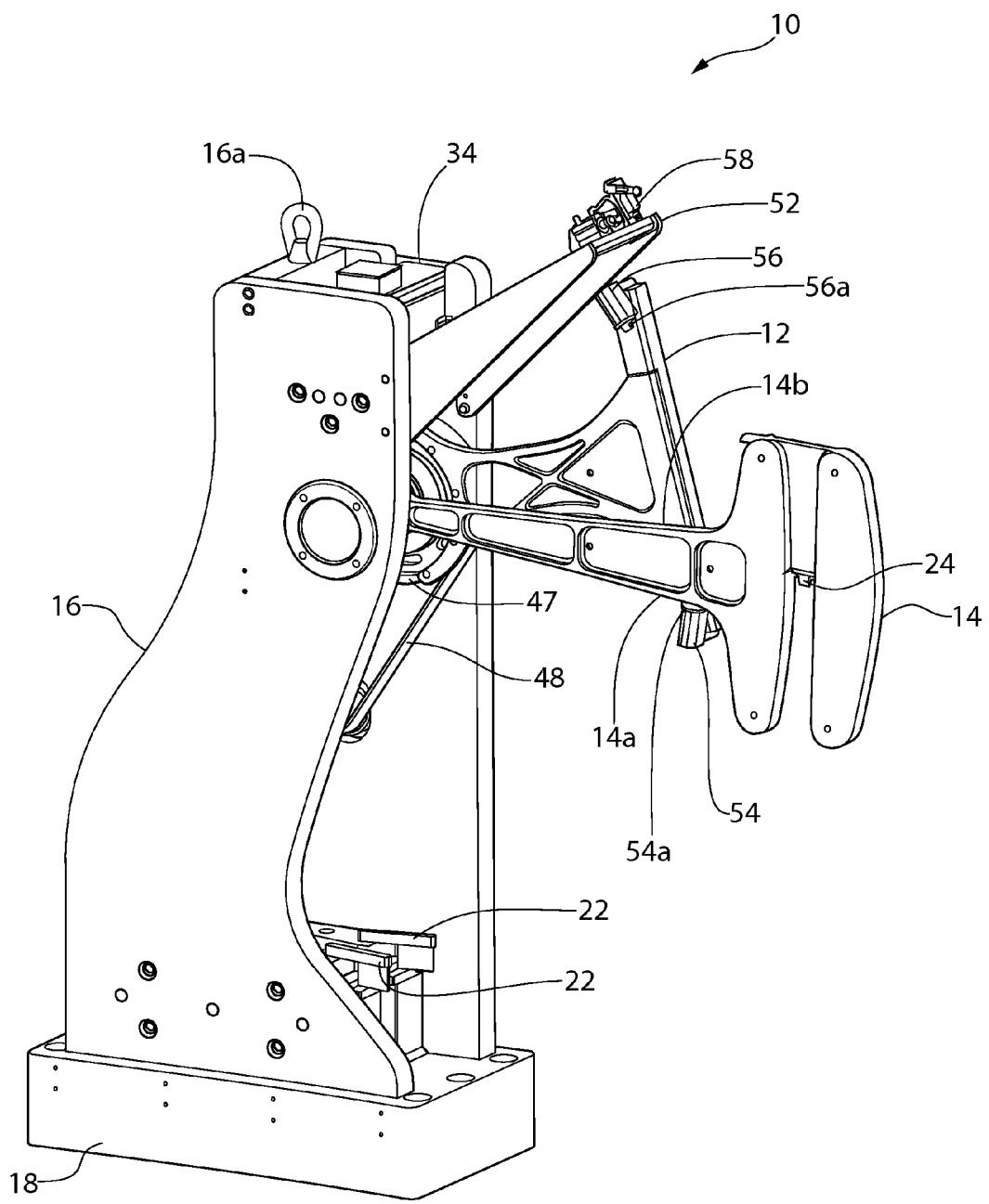
FIG. 7 is a front, left, top isometric view of the impact tester of FIG. 1 shown with the pendulum stopped between the latch position and the impact position by the safety return arm.

Referring to FIG. 3, safety return arm 12 may include a lift member 54. Lift member 54 may be configured to engage pendulum 14 to lift pendulum 14 to an initial or latched position and/or to stop pendulum 14 between the latched position and the impact position at various positions along the swing path of pendulum 14. In one embodiment, lift member 54 extends axially (generally parallel to axis $A_1$) to intersect the plane that pendulum 14 swings on so that lift member 54 travels on the same plane or swing path as pendulum 14. As pendulum 14 swings, lift member 54 is controlled to stay radially spaced from pendulum 14. Upon command, safety return arm 12 shifts angularly relative to pendulum 14 or stops rotating such that lift member 54 contacts a left side surface 14a of pendulum 14 in the lift and top positions. In other embodiments, lift member 54 is configured to contact another portion of pendulum 14.

Lift member 54 may include a bumper 54a that softens the interface between lift member 54 and pendulum 14. In one embodiment, bumper 54a is comprised of an elastomeric material. In another embodiment, left side surface 14a may include or be coated with an elastomeric material.

Safety return arm 12 may additional or alternatively include a stop member 56. Stop member 56 may be configured to engage pendulum 14 to stop and/or hold pendulum 14 during a backswing. In one embodiment, stop member 56 extends axially (generally parallel to axis $A_1$) to intersect the plane that pendulum 14 swings on so that stop member 56 travels on the same plane or swing path as pendulum 14. As pendulum 14 swings, stop member 56 is controlled to stay radially spaced from pendulum 14. Upon command, safety return arm 12 shifts angularly relative to pendulum 14 or stops rotating such that stop member 56 contacts a left side surface 14b of pendulum 14 during a backswing of pendulum 14. In other embodiments, stop member 56 is configured to contact another portion of pendulum 14.

Stop member 56 may include a bumper 56a that softens the interface between stop member 56 and pendulum 14. In one embodiment, bumper 56a is comprised of an elastomeric material. In another embodiment, left side surface 14b may include or be coated with an elastomeric material.

Stop member 56 and lift member 54 may be generally radially aligned on opposing sides of pendulum 14. In other embodiments, stop member 56 is radially offset from lift member 54. Stop member 56 may be spaced from lift member 54 a distance greater than the width of pendulum 14 where safety return arm 12 contacts pendulum 14. The distance between stop member 56 and safety return arm 12 may be to allow for any delay in using sensors 26, 30 so that safety return arm 12 does not inadvertently contact pendulum 14 during use.

In other embodiments, the inverse configuration of safety return arm 12 and pendulum 14 may be used where pendulum 14 includes an axially extending component (generally parallel to axis $A_1$) that extends through a plane that the safety return arm 12 swings on. In other embodiments, pendulum 14 or safety return arm 12 may include an axially extending projection (generally parallel to axis $A_1$) that extends through an aperture in safety return arm 12 or pendulum 14.

Referring to FIG. 1, impact tester 10 may include a latch arm 52. Latch arm 52 may be configured to retain pendulum 14 in the initial or latched position. Latch arm 52 may include a latch 58 configured to releaseably retain a keeper 60 mounted on the distal end of pendulum 14. A pneumatic cylinder 62 may be actuated by a latch release solenoid valve on command by control mechanism 28. In other embodiments, latch arm 52 includes another retention mechanism such as a magnet. In other embodiments, latch arm 52 is omitted and safety return arm 12 acts as the retention mechanism to retain pendulum 14 in the initial position.

During use, in an exemplary embodiment, pendulum 14 begins in the initial position after being lifted by safety return arm 12 (see FIG. 3). Safety return arm 12 is then pivoted about axis $A_1$ by control mechanism 28 and motor 34 to a neutral position with lift member 54 and stop member 56 spaced from either side of pendulum 14 so that lift member 54 is not contacting pendulum 14 (see FIG. 4). Impact tester 10 is now is the latched and ready for test position. Once the test specimen is in place and the command is given to control mechanism 28, latch 58 releases pendulum 14 and pendulum 14 falls due to the force of gravity acting on the distal end of pendulum 14 toward the impact position (see FIG. 5). Using the sensors 30, 26 to determine the position of safety arm 12 relative to pendulum 14, control mechanism 28 and motor 34 pivot safety return arm 12 to follow the swing of pendulum 14 without touching pendulum 14. Pendulum 14 then contacts the test specimen (see FIG. 1) and, depending on the type of test, breaks through the test specimen and continues swinging (see FIG. 6) to a post-impact position or bounces off the test specimen back toward the latched position in a post-impact position. The resulting movement of pendulum 14 is sensed by second sensor 26 and recorded. Whether pendulum 14 breaks through or off of test specimen, pendulum 14 may be stopped in the post-impact position by safety return arm 12. Safety return arm 12 is then pivoted such that lift member 54 contacts right side surface 14a of pendulum 14 and lifts pendulum back up to the latched position such that impact tester 10 is ready for a subsequent test. If desired (e.g., user presses a stop button or to protect a subsequent impact to the specimen) or necessary out of a sensed safety concern (e.g., motion sensor detects an object within the swing path), pendulum 14 may be stopped mid-swing, in either a forward swing or a backward swing (see FIG. 7), and reset to the initial position.

Figure 8A:
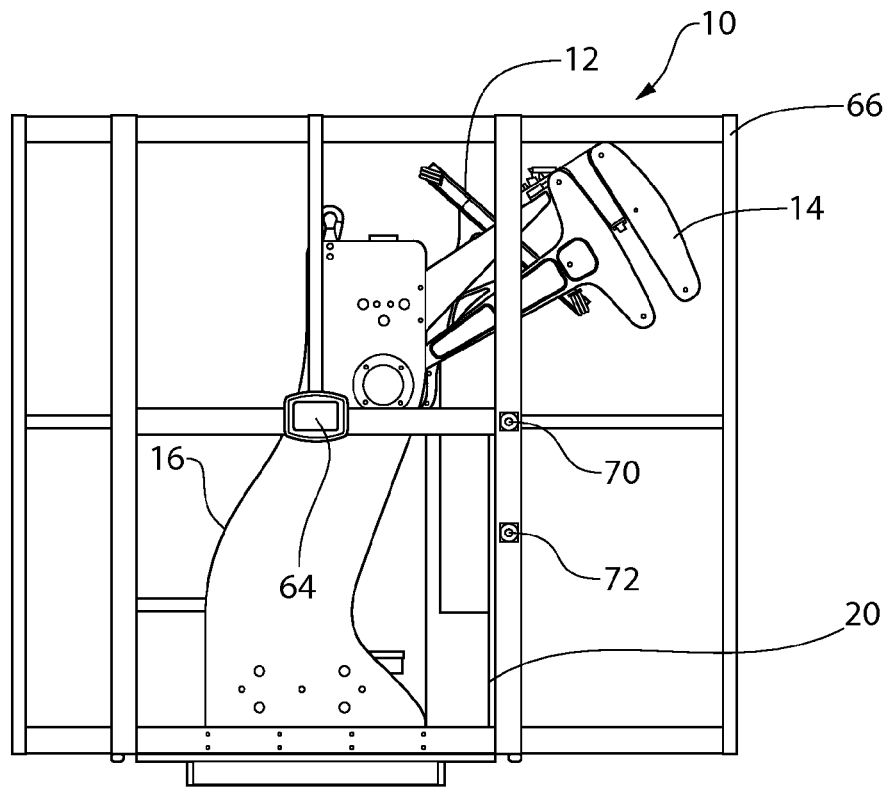
FIG. 8A is a front elevational view of the impact tester of FIG. 1 shown within a safety enclosure.
Figure 8B:
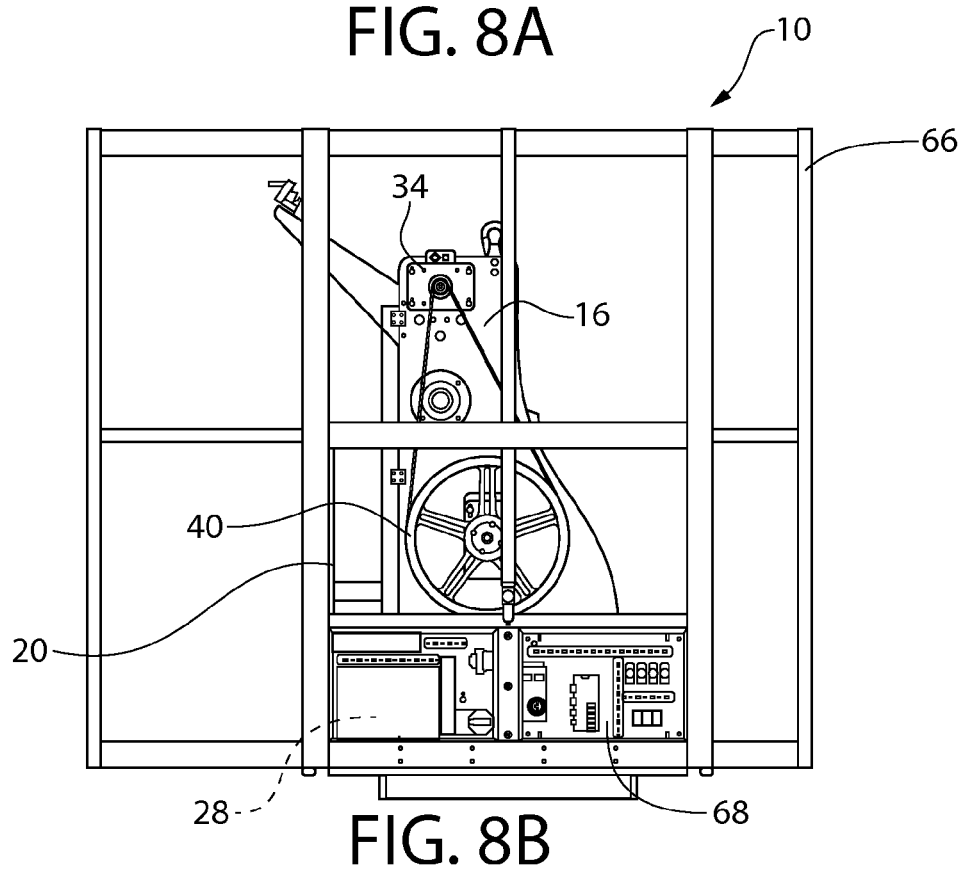
FIG. 8B is a rear elevational view of the impact tester of FIG. 1 shown within a safety enclosure.

Referring to FIGS. 8A-8B, impact tester 10 may be partially or fully enclosed by a safety enclosure 66. Safety enclosure 66 may be configured to prevent a user from being within the swing path of pendulum 14 and from being hit by fragments from the test specimen. In one embodiment, safety enclosure 66 is an acrylic enclosure with an aluminum frame. Access to the front of impact tester 10 may be unimpeded by safety enclosure 66. In other embodiments, safety enclosure 66 extends around the entire perimeter of impact tester 10. Access to the test specimen, such as through the front of impact tester 10, may be monitored by one or more motion sensors 20. Motion sensor 20 may be a light curtain that at least partially surrounds the swing path of pendulum 14. The light curtain may include a plane that a user needs to cross to access the test specimen such as a front plane as shown in FIG. 8A. In other embodiments, motion sensor 20 is any sensor configured to detect the presence of an object proximate impact tester 10 such as infrared, ultrasonic or microwave. In one embodiment, when motion sensor 20 senses an object, control mechanism 28 interrupts any release signals from being sent to pneumatic cylinder 62 to release the solenoid valve and, if pendulum 14 has been released, sends a signal to interrupt power to motor 34 and causes safety return arm 12 to stop and impede pendulum 14 from swinging. Motor 34 may contain a fail-safe brake that engages and prevents motor 34 from spinning when power is removed from motor 34.

One or more emergency stop push buttons 70 may be mounted on safety enclosure 66 that will interrupt the circuit to the latch release solenoid valve and sends a signal to control mechanism 28 when push button 70 is pressed. A release button 72 may be mounted on the safety enclosure 66 to provide a signal to control mechanism to begin test by releasing pendulum 14. Stop push button 70 and release push button 72 may use separate circuits for added safety.

Impact tester 10 may include a user interface 64 that a user can input commands and program control system 28. In addition, user interface 64 may be configured to calculate test results and displays the results to the user. In one embodiment, user interface 64 is a touch screen. In one embodiment, user interface 64 is configured to recognize speech commands such as "stop" to stop pendulum 14 with safety return arm 12. An electrical enclosure 68 may be used, such as on the rear of impact tester 10, to enclose control mechanism 28 and associated electronics.

Figure 9:
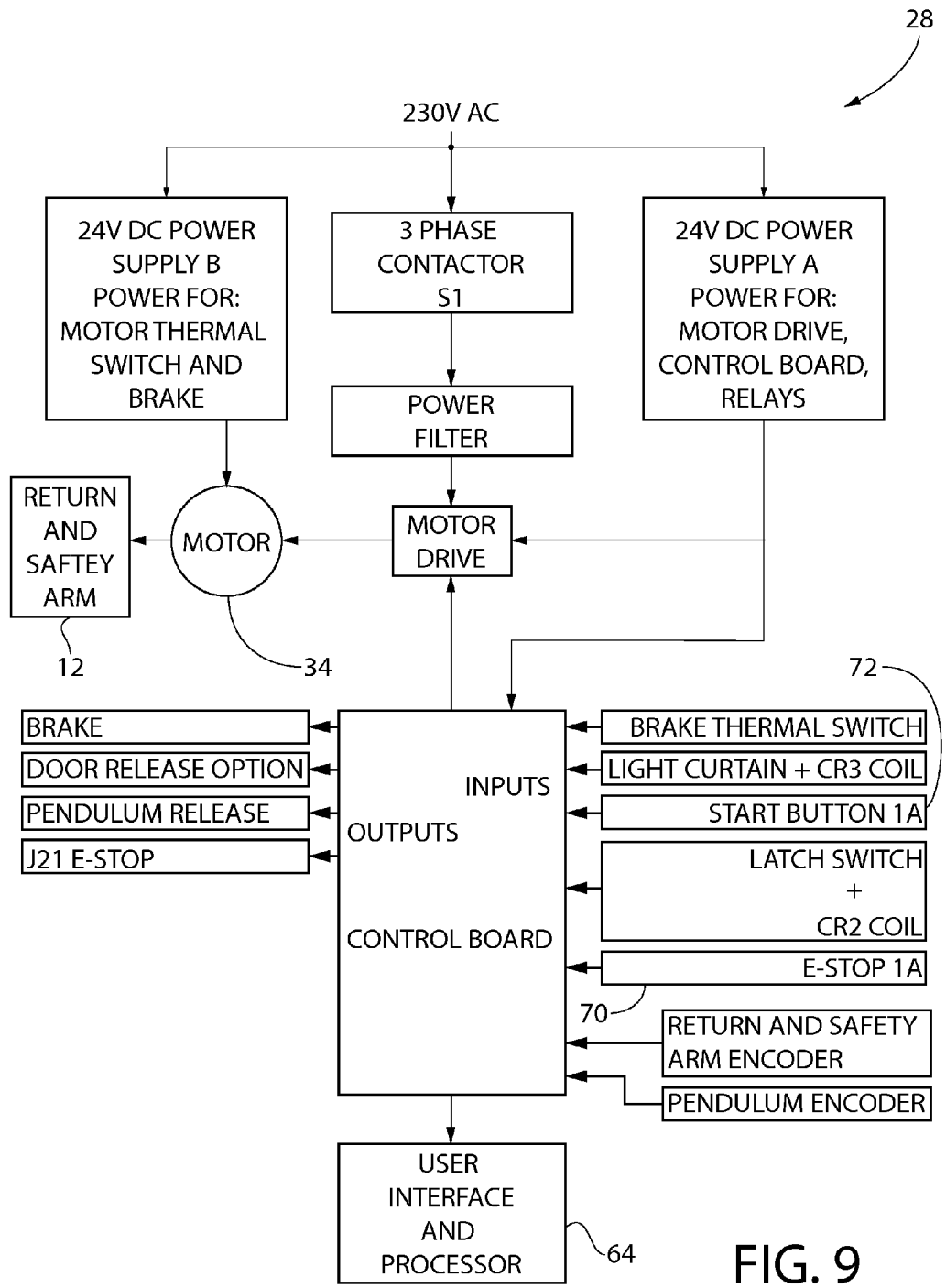
FIG. 9 is a block diagram of the electrical connections for the impact tester of FIG. 1.

Referring to FIG. 9, an exemplary electronic schematic is shown. Impact tester 10 may include a power supply such as two 24 volt power supplies for control circuitry, a controller for the light curtain, and the control microprocessor. In one embodiment, impact tester 10 includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, operate impact tester 10 and/or perform one or more of the methods disclosed herein.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. An impact tester comprising:
a pendulum rotatable about a first axis from a latched position to an impact position, the pendulum configured to impact a test specimen in the impact position; and
a safety return arm rotatable about a second axis generally parallel to the first axis, the safety return arm configured to lift the pendulum to the latched position, allow the pendulum to swing from the latched position toward the impact position, and selectively stop the pendulum between the latched position and the impact position, the safety return arm having a lift member configured to engage a left side surface of the pendulum when lifting and stopping the pendulum, the left side surface facing toward the test specimen in the latched position.

2. The impact tester of claim 1 further comprising:
a motor configured to control an angular position of the safety return arm.

3. The impact tester of claim 2 further comprising:
a first sensor configured to measure an angular position of the pendulum;
a second sensor configured to measure an angular position of the safety return arm; and
a control system configured to control the angular position of the pendulum using the safety return arm based on the angular position of the pendulum and the angular position of the safety return arm.

4. The impact tester of claim 3 further comprising:
a frame supporting the pendulum and the safety return arm, wherein the first sensor is configured to measure the angular position of the pendulum relative to the frame.

5. The impact tester of claim 4, wherein measurements from the first and second sensors are used to determine the position of the safety return arm relative to the pendulum.

6. The impact tester of claim 3, wherein the second sensor is configured to measure the position of the safety return arm relative to the frame.

7. The impact tester of claim 3 further comprising:
a user interface configured to control the control system.

8. The impact tester of claim 1, wherein the lift member includes an elastomeric bumper.

9. The impact tester of claim 1, wherein a proximal end of the safety return arm is axially spaced from a proximal end of the pendulum and the lift member travels on the same plane as the pendulum.

10. The impact tester of claim 1, wherein the safety return arm includes a stop member that is configured to engage a right side surface of the pendulum and limit the pendulum from swinging back toward the latch position after impacting the test specimen, the right side surface facing away from the test specimen in the impact position.

11. The impact tester of claim 10, wherein the stop member includes an elastomeric bumper.

12. The impact tester of claim 10, wherein the stop member and the pendulum travel on the same plane.

13. The impact tester of claim 1 further comprising:
a sensor configured to detect the presence of an object proximate a swing path of the pendulum.

14. The impact tester of claim 13, wherein the sensor is a light curtain.

15. The impact tester of claim 1, wherein the pendulum is rotatable about the first axis from the latched position through the impact position to a post-impact position and wherein the safety return arm is configured to selectively stop the pendulum between the latched position and the post-impact position.

16. The impact tester of claim 1, wherein the first axis is coaxial with the second axis.

17. The impact tester of claim 1, wherein the pendulum is configured to perform Charpy impact testing of the test specimen.

18. The impact tester of claim 1, wherein the pendulum is configured to perform Izod impact testing of the test specimen.

19. The impact tester of claim 1, wherein the pendulum includes a crosshead configured to perform tension impact testing of the test specimen.

20. The impact tester of claim 1, wherein the pendulum is configured to perform shear impact testing of the test specimen.

21. An impact tester comprising:
a pendulum rotatable about a first axis from a latched position to an impact position, the pendulum configured to impact a test specimen in the impact position; and
a safety return arm rotatable about a second axis generally parallel to the first axis, the safety return arm including a lift member configured to engage a left side surface of the pendulum, the left side surface facing toward the test specimen in the latched position, the safety return arm including a stop member configured to engage a right side surface of the pendulum, the right side surface facing away from the test specimen in the impact position,
wherein the lift member and the stop member extend toward one another and are both spaced from the pendulum in the latched position, and
wherein the lift member, the stop member, and the pendulum travel on the same plane.

22. An impact tester comprising:
a pendulum rotatable about a first axis from a latched position to an impact position, the pendulum configured to impact a test specimen in the impact position; and
a safety return arm rotatable about a second axis generally parallel to the first axis, the safety return arm configured to lift the pendulum to the latched position, allow the pendulum to swing from the latched position toward the impact position, and selectively stop the pendulum between the latched position and the impact position;
a motor configured to control an angular position of the safety return arm;
a first sensor configured to measure an angular position of the pendulum;
a second sensor configured to measure an angular position of the safety return arm; and
a control system configured to control the angular position of the pendulum using the safety return arm based on the angular position of the pendulum and the angular position of the safety return arm.

23. The impact tester of claim 22 further comprising:
a frame supporting the pendulum and the safety return arm, wherein the first sensor is configured to measure the angular position of the pendulum relative to the frame.

24. The impact tester of claim 23, wherein measurements from the first and second sensors are used to determine the position of the safety return arm relative to the pendulum.

25. The impact tester of claim 23, wherein the second sensor is configured to measure the position of the safety return arm relative to the frame.

26. The impact tester of claim 23 further comprising:
a user interface configured to control the control system.

* * * * *